United States Patent
Seck et al.

(10) Patent No.: US 8,372,165 B1
(45) Date of Patent: Feb. 12, 2013

(54) DIESEL AND JET FUEL COMPOSITIONS CONTAINING THE OXYGENATED COMPOUND 1,2-(DITETRAHYDROFURYL)ETHANE DERIVED FROM RENEWABLE FURFURAL

(76) Inventors: Karl A. Seck, Ferndale, WA (US); Edwin S. Olson, Grand Forks, ND (US)

( * ) Notice: Subject to any disclaimer, the term of this patent is extended or adjusted under 35 U.S.C. 154(b) by 0 days.

(21) Appl. No.: 12/984,363

(22) Filed: Jan. 4, 2011

Related U.S. Application Data

(60) Provisional application No. 61/335,209, filed on Jan. 4, 2010.

(51) Int. Cl.
*C10L 1/185* (2006.01)
(52) U.S. Cl. ............................................. 44/352; 127/37
(58) Field of Classification Search .................... 44/352; 127/37
See application file for complete search history.

(56) References Cited

U.S. PATENT DOCUMENTS

| | | | |
|---|---|---|---|
| 7,671,246 B2 * | 3/2010 | Dumesic et al. | 585/240 |
| 7,880,049 B2 * | 2/2011 | Dumesic et al. | 585/733 |
| 2003/0154975 A1 * | 8/2003 | Lightner | 127/37 |

FOREIGN PATENT DOCUMENTS

| | | | |
|---|---|---|---|
| EP | 2034005 | * | 3/2009 |
| WO | WO 2007/146636 | * | 12/2007 |

* cited by examiner

*Primary Examiner* — Cephia D Toomer
*Assistant Examiner* — Monique Cole

(57) ABSTRACT

A diesel fuel blending component primarily comprised of 1,2-(ditetrahydrofuryl)ethane (DTHFE) along with a method of manufacture is presented. The blending component will reduce PM and other emissions in a diesel engine. The component is manufactured from C5 sugar sources by first converting to furfural, then furion, and then hydrotreated to the desired product.

7 Claims, 1 Drawing Sheet

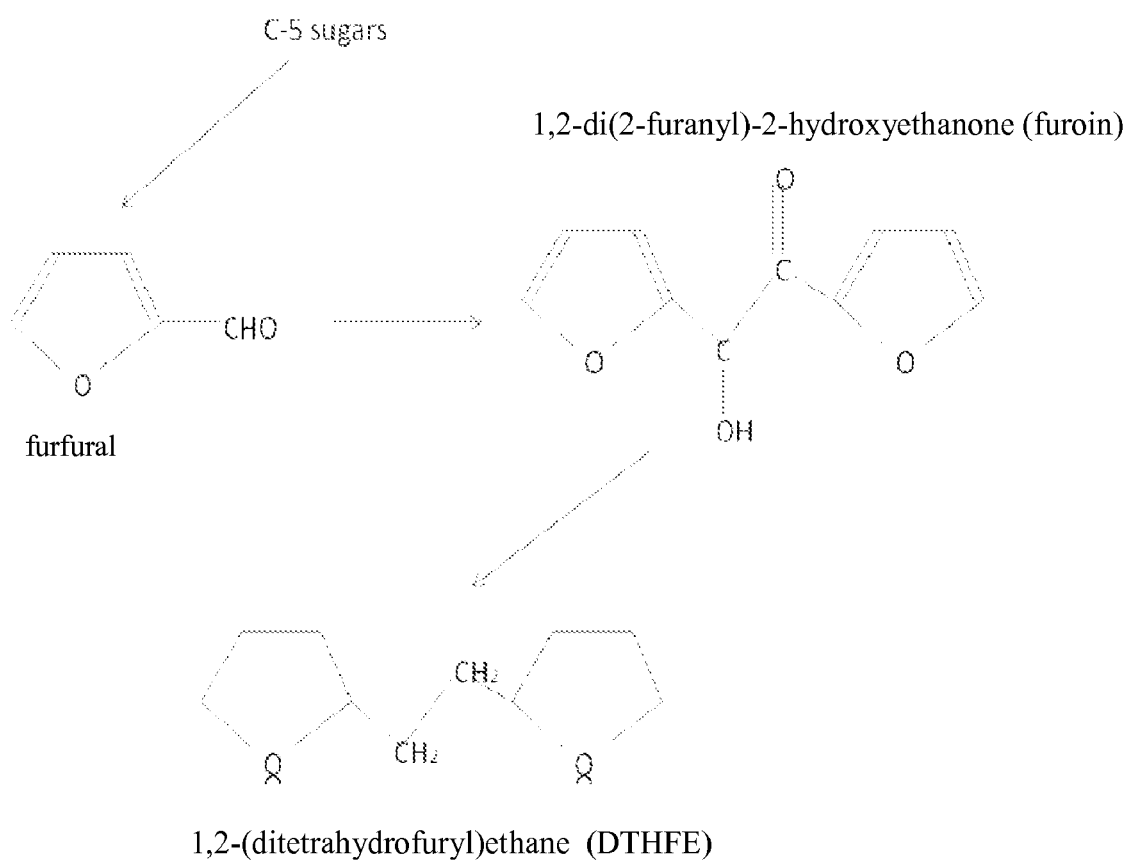

DIESEL AND JET FUEL COMPOSITIONS CONTAINING THE OXYGENATED COMPOUND 1,2-(DITETRAHYDROFURYL)ETHANE DERIVED FROM RENEWABLE FURFURAL

RELATED APPLICATIONS

This application claims the benefits of U.S. Provisional Patent Application No. 61/335,209 filed on Jan. 4, 2010.

FIELD OF THE INVENTION

The invention relates to diesel and other fuel compositions containing the oxygenated compound 1,2-(ditetrahydrofuryl) ethane derived from renewable furfural.

BACKGROUND OF THE INVENTION

Today, global climate change and energy national security as well as improvement of air quality are an absolute global priority. Most cellulosic biofuels technologies are designed to produce gasoline blendstocks such as ethanol. Diesel cellulosic oxygenated fuels would reduce greenhouse emissions as well as limit the precursors of some pollutants, such as particles, and compounds which react with tropospheric ozone or toxic compounds. A cellulosic fuel that is a viable turbine fuel with application to the renewable jet fuel market would also be of great benefit for climate change mitigation and energy national security.

SUMMARY OF THE INVENTION

It is one of the objects of the invention to propose the use of the oxygenated compound 1,2-(ditetrahydrofuryl)ethane derived from renewable furfural as additives or formulation bases of diesels and jet fuels leading to a significant lowering of particle emissions and lifecycle analysis greenhouse gases.

BRIEF DESCRIPTION OF THE DRAWING

FIG. 1 Synthesis of 1,2-(ditetrahydrofuryl)ethane.

DETAILED DESCRIPTION

The compound 1,2-(ditetrahydrofuryl)ethane (DTHFE) is prepared in high yield from lignocellulosic biomass and used as a blending component for renewable diesel and jet fuel blends. DTHFE general formula is depicted as:

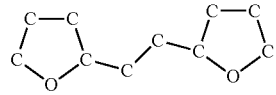

Process for the conversion of pentose feedstocks to a high cetane diesel fuel additive, comprising the following steps:

A. Thermal reaction of the hemicellulosic byproduct to furfural

B. Self-condensation of the furfural intermediate to furoin

C. Catalytic hydrogenation of the furoin to 1,2-(ditetrahydrofuryl)ethane.

A summary of the reaction steps is depicted in FIG. 1.
Synthesis of 1,2-(ditetrahydrofuryl)ethane.

Furfural Feedstock

Furfural has traditionally been obtained from thermal processing of 5-carbon sugars, available from the hemicellulose fraction of biomass wastes. Large amounts of furfural were produced from oat hulls, corn cobs and stalks, and other agricultural byproducts. In the future, furfural will be derived from pulping wastes and other lignocellulose conversion processes. The preferred embodiment is a process whereby solubilized hemicellulosic byproducts are separated from cellulose solids and subsequently lignin byproduct and converted to furfural in a continuous process using a solid acid catalytic bed. Concentration of the furfural is accomplished by simple distillation.

Furoin Synthesis

The self condensation of furfural to 1,2-di(2-furanyl)-2-hydroxyethanone (furoin) is a known variant of the acyloin condensation, wherein C—C bonds are formed from aldehyde substrates by joining at the aldehyde carbons. Catalysts for the reaction are potassium cyanide and various heterocyclics including triazolium, imidazolium, and thiazolium salts, such as vitamin B1. Either cyanide or heterocyclic catalysts can be utilized in a solid catalyst bed in a continuous reactor, or in a batch mode, facilitating separation and removal of the catalyst from the reaction products. Reuse of the catalyst has been demonstrated.

KCN catalyst gives good yields with benzaldehyde, but poor yields with furfural. A quaternary resin bound form of cyanide also gave good yields with benzaldehyde (1), but a polymer resin form of the cyanide gave poor yields with furoin (2).

Improved yields of furoin have been reported using heterocyclic catalysts. Thiazolium salts have been utilized successfully for furfural condensations for some time (3). Thiazolium polymers gave high yields of furoin (4). Imidazolium salts are essentially an ionic liquid and with added base form an effective carbene catalyst for furfural condensation (5-7). Attaching the imidazolium catalyst to a polymer support resulted in a stable catalyst that could be easily separated (8). Triazolium salts also gave good results, but the catalysts are more difficult to synthesize (9). Since any of these heterocyclic catalysts could be affixed to a polystyrene bead, construction of a fixed bed reactor for the furoin synthesis is a feasible alternative. The preferred embodiment is the thiazole-substituted polystyrene catalyst which gives high yields of furoin and the catalyst is easily recovered.

Hydrotreating.

Furoin is reduced in the final step to 1,2-(ditetrahydrofuryl) ethane. This is accomplished by catalytic hydrogenation at an elevated temperature. Reduction of both the oxygen functionality and the furan rings is desired, so there is no concern about selectivity. Thus effective reduction of both moieties is obtained with platinum, palladium, nickel, rhodium, and ruthenium. With platinum, hydrogenolysis (ring opening) of the tetrahydrofuran rings occurs, giving polyalcohol products. Reduction with Raney nickel at moderate temperatures gives high yields of furan hydrogenation to the desired tetrahydrofuran moieties without ring opening.

Fuel Blending

For diesel fuels for compression ignition engines, in one embodiment, the DTHFE is used as an additive to improve cetane and cold flow properties of petroleum diesel or biodiesel (FAME) blends. Percentages considered additive blend levels of DTHFE are 0.1% to 5%. Blends in this range would also reduce exhaust particulates. In another embodiment, blends from 5% to 80% would add additional renewable content to the fuel and maintain the advantages of the additive blend levels. Most probably 10% to 30% blends would be used.

DTHFE blends with petroleum kerosene would provide renewable content to jet fuels without compromising freeze point and smoke point and other critical specifications. Blend ranges could be from 5% to 80%.

EXAMPLE 1

The condensation of furfuraldehyde to furoin was conducted with a catalyst comprising thiamine anion. The catalyst was prepared by dissolving 0.05 moles (17 g) 5-(2'-hydroxyethyl)-4-methylthiazole hydrochloride in 100 mL of water in a one liter flask. To the stirred solution, 300 mL of 95% ethanol was added and the solution was cooled. A cold solution of sodium hydroxide (63 mL of 5 N) was slowly added to the ethanolic thiamine solution while stirring in the cold bath. The excess of base produced the yellow thiamine anion solution which was allowed to warm to room temperature. Furfural (1.0 moles, 96 g) was added to the catalyst solution and stirred briefly. After standing 24 hours, crystals of furoin were collected by filtration, washed with a small amount of water, and air dried. Weight of furoin was 89 g (melting point 130 C.). The impure crystals dissolved in hot ethanol, methylTHF and diglyme.

This product was used in the subsequent hydrotreating step without further purification. The catalyst solution filtrate was reused without any regeneration step needed. That is, furfural was added, and the solution was stirred and allowed to stand, whereupon a similar yield of crystalline furoin was obtained. The filtrate was reused four times.

EXAMPLE 2

The condensation of furfuraldehyde to furoin was conducted with a solid catalyst comprising the thiamine anion supported on a quaternary ammonium anion exchange resin. The catalyst was prepared by dissolving 0.005 moles of 5-(2'-hydroxyethyl)-4-methylthiazole hydrochloride in 10 mL of water in a one liter flask. To the stirred solution, 30 mL of 95% ethanol was added and the solution was cooled. The anion exchange resin (50 g) in the hydroxide form was added and stirred for several hours. Furfural (5 g) was added and the slurry allowed to stand for 24 hr. Furoin was removed from the resin-supported thiamine with hot ethanol. Crystallization gave 3 g of impure furoin.

What is claimed is:

1. A method of producing a fuel additive for reducing diesel engine emissions, said method comprising the steps of:
    a.) reacting at least one C5 sugar through an acid catalyst reactor system to convert said C5 sugar to furfural;
    b.) reacting said furfural from a.) through a catalyst reactor system to self-condense said furfural into 1,2-di(2-furanyl)-2-hydroxyethanone (furoin); and
    c.) reacting said furoin from b.) with hydrogen through a solid heterogeneous catalyst bed reactor system to hydrogenate said 1,2-di(2-furanyl)-2-hydroxyethanone (furoin) into 1,2-(ditetrahydrofuryl)ethane (DTHFE).

2. A The method of claim 1, wherein said at least one C5 sugar is obtained from the group consisting of:
    C5 syrup from cellulosic ethanol manufacturing plants;
    fruit processing waste;
    oat hulls;
    corn cobs and stalks;
    other agricultural byproducts;
    wood pulping and other hemicellulosic byproducts; and
    combinations thereof.

3. The method of claim 1, wherein the step of reacting said furfural through a catalyst reactor system comprises:
    reacting said furfural through a solid heterogeneous catalyst bed reactor system.

4. The method of claim 3, wherein said solid heterogeneous catalyst bed reactor system comprises of a catalyst selected from the group consisting of:
    polymer resin form of KCN;
    thiazolium salts
    thiazolium polymers;
    thiazole-substituted polystyrene; and
    combinations thereof.

5. The method of claim 1, wherein the step of reacting said furfural through a catalyst reactor system comprises:
    reacting said furfural through a liquid catalyst system.

6. The method of claim 5, wherein said liquid catalyst reactor system comprises:
    a liquid thiamine anion solution catalyst.

7. The method of claim 1, wherein said solid heterogeneous catalyst bed reactor system through which said furoin is reacted with hydrogen comprises a catalyst selected from the group consisting of:
    platinum;
    palladium;
    nickel;
    rhodium,
    ruthenium; and
    combinations thereof.

* * * * *